United States Patent
Bender et al.

(10) Patent No.: US 6,181,426 B1
(45) Date of Patent: Jan. 30, 2001

(54) GAS CONCENTRATION MONITORING SYSTEM

(75) Inventors: Gerald M. Bender, St. Louis; Loyal B. Shawgo, St. Charles, both of MO (US)

(73) Assignee: McDonnell Douglas Corporation, St. Louis, MO (US)

(*) Notice: Under 35 U.S.C. 154(b), the term of this patent shall be extended for 0 days.

(21) Appl. No.: 09/054,483

(22) Filed: Apr. 3, 1998

(51) Int. Cl.[7] ............................................. G01N 21/00
(52) U.S. Cl. .................................. 356/432; 356/437
(58) Field of Search ............................. 356/437, 432; 250/339.13, 343, 345; 73/31.05

(56) References Cited

U.S. PATENT DOCUMENTS

| | | | |
|---|---|---|---|
| 3,677,652 | 7/1972 | Little | 356/183 |
| 4,281,248 * | 7/1981 | Fabinski et al. | 250/345 |
| 5,059,953 | 10/1991 | Parsons et al. | 340/578 |
| 5,222,389 * | 6/1993 | Wong | 356/437 |
| 5,281,816 | 1/1994 | Jacobson et al. | 250/339 |
| 5,340,986 * | 8/1994 | Wong | 356/437 |
| 5,341,214 * | 8/1994 | Wong | 356/437 |
| 5,387,979 | 2/1995 | Brauer et al. | 356/435 |
| 5,429,805 * | 7/1995 | Uno et al. | 250/339.13 |
| 5,486,699 * | 1/1996 | Fabinski et al. | 250/345 |
| 5,515,859 | 5/1996 | Paz | 128/719 |
| 5,625,189 * | 4/1997 | McCaul et al. | 356/437 |
| 5,689,114 * | 11/1997 | Miyazaki et al. | 250/345 |
| 5,693,945 * | 12/1997 | Akiyama et al. | 250/339.13 |

* cited by examiner

*Primary Examiner*—Robert Kim
(74) *Attorney, Agent, or Firm*—Westerlund & Powell, P.C.

(57) ABSTRACT

A system for monitoring the concentration level of a gas in a monitored environment, e.g., for monitoring the concentration level of a fire suppression agent in the engine bay and/or cargo bay of an aircraft. The system includes a light source for producing source light, an optical system that directs the source light along a plurality of different optical paths having different respective optical path lengths, and a plurality of photodetectors that are positioned to receive the source light that traverses different respective ones of the plurality of different optical path lengths, and which produce a plurality of output signals indicative of the concentration level of the gas in the monitored environment. In the preferred embodiment, the system further includes a narrow band spectral filter positioned between the light source and each photodetector, wherein the narrow band spectral filter has a narrow band pass that is matched to a selected optical absorption wavelength of the gas.

16 Claims, 2 Drawing Sheets

GAS CONCENTRATION MONITORING SYSTEM

BACKGROUND OF THE INVENTION

The present invention relates generally to the technology for measuring the levels or concentration of a gas in a monitored environment, and, more particularly, to a gas concentration measurement technique and system that is useful for remotely monitoring the concentration of a fire suppression agent such as HALON within military and commercial aircraft engine bays and cargo compartments.

The recent crash in Florida of a Valujet aircraft has stimulated discussion that might lead to FAA requirements for fire suppression equipment in commercial aircraft cargo holds. Presently, HALON is the primary fire suppression agent used in military and commercial aircraft. However, since halons are the worst known ozone-depleting chemicals (ODCs), alternative fire suppression agents are currently being sought.

In general, existing fire suppression systems include a fire suppression agent distribution system that distributes the fire suppression agent to the aircraft engine bays and selected cargo compartments. In a typical application, in order to effectively extinguish a fire, concentrations of fire suppression agent must be in excess of 6% for a period of 0.5 seconds. Lower concentrations or shorter time periods reduce effectiveness, and conversely, higher concentrations and/or longer time periods waste suppression. Additionally, oversizing the system can result in toxic concentrations with some fire suppression agents.

Typically, the fire suppression system undergoes a ground-based certification or qualification testing procedure in which the concentration of the fire suppression agent within the environments where the agent is distributed, i.e., within the aircraft engine bays and cargo compartments, is determined, in order to confirm proper operation of the fire suppression system. However, this procedure only certifies the proper operation of the fire suppression system prior to flight. None of these gas concentration measurement systems that are used in pre-flight certification testing of fire suppression systems are capable of being flown on the aircraft to monitor the concentration of the fire suppression agent during flight (e.g., during operation of the fire suppression system), in order to verify proper operation of the fire suppression system when it is activated and/or to provide feedback data that could enable the level of the fire suppression agent to be dynamically adjusted as required to ensure safe, effective, efficient, and reliable operation of the fire suppression system.

In this connection, the presently available gas concentration measurement systems that are used in pre-flight certification testing of fire suppression systems, such as the Pacific Scientific Halonizer, are generally undesirably complex, bulky, and expensive, and further, are either limited in the number of sample positions that can be monitored simultaneously, or are very slow, thereby limiting the accuracy or speed, respectively, of the gas concentration monitoring system, and thus, the safety, effectiveness and efficiency of the associated fire suppression system. For instance, the Pacific Scientific Halonizer, which was designed to monitor HALON concentrations for certification/qualification of aircraft fire suppression systems, has high data rates, but can only monitor four sample positions. Another device used by Pacific Scientific can multiplex twenty sample positions (via an electro-mechanical sampling system), but the sample rate for any one position is approximately only one sample every two seconds (i.e., 30 samples/minute).

Based on the above, it can be appreciated that there presently exists a need in the art for a fire suppression agent gas concentration monitoring system that overcomes the drawbacks and shortcomings of the presently available technology, and which is preferably capable of being flown on an aircraft. More particularly, there presently exists a need for a fire suppression agent gas concentration monitoring system that is fast and accurate, yet also small, low-cost, and reliable. Ideally, such a gas concentration monitoring system should have a large dynamic range and be implemented as a single, compact device. The present invention meets these objectives and fullfills this need in the art.

SUMMARY OF THE INVENTION

The present invention encompasses, in one of its aspects, a system for monitoring the concentration level of a gas in a monitored environment, e.g., for monitoring the concentration level of a fire suppression agent in the engine bay and/or cargo bay of an aircraft. The system includes a light source for producing source light, an optical system that directs the source light along a plurality of different optical paths having different respective optical path lengths, and a plurality of photodetectors that are positioned to receive the source light that traverses different respective ones of the plurality of different optical path lengths, and which produce a plurality of output signals indicative of the concentration level of the gas in the monitored environment. In the preferred embodiment, the system further includes a narrow band spectral filter positioned between the light source and each photodetector, wherein the narrow band spectral filter has a narrow band pass that is matched to a selected optical absorption wavelength of the gas.

The present invention encompasses, in another of its aspects, a system for monitoring the concentration level of a gas in a monitored environment that includes a source of monochromatic light having a wavelength that is the same as a selected optical absorption wavelength of the gas, an optical system that directs the light along a plurality of different optical paths having different respective optical path lengths, and a detection system that detects the light that traverses each different optical path length, and that produces a plurality of output signals indicative of the concentration level of the gas in the monitored environment.

The present invention encompasses, in yet another of its aspects, a method for monitoring the concentration level of a gas in a monitored environment, that includes the steps of directing light along a plurality of different optical paths having different respective optical path lengths, filtering the light to pass only a prescribed spectral band which includes an optical absorption wavelength of the gas, and detecting the filtered light that traverses each different optical path length, and producing a plurality of output signals indicative of the concentration level of the gas in the monitored environment.

The present invention encompasses, in yet another of its aspects, a method for monitoring the concentration level of a gas in a monitored environment, that includes the steps of producing monochromatic light having a wavelength that is the same as a selected optical absorption wavelength of the gas, directing the light along a plurality of different optical paths having different respective optical path lengths, and detecting the light that traverses each different optical path length, and producing a plurality of output signals indicative of the concentration level of the gas in the monitored environment.

BRIEF DESCRIPTION OF THE DRAWINGS

These and various other features, objects, and advantages of the present invention will become more clearly apparent from the following detailed description read in conjunction with the accompanying drawings, in which.

DETAILED DESCRIPTION OF THE INVENTION

The design and operation of the gas concentration monitoring system of the present invention described below is based upon the following scientific principles. In general, a gas to be monitored ("the monitored gas") has a characteristic optical absorption line(s). For example, CF3I and HF-25 (which are two of the candidate replacements for HALON) have absorption lines at approximately 8.3–8.5 micrometers, and CF3I has a strong absorption line at 9.3–9.4 micrometers, and another strong absorption line at 13.9 micrometers. Optical radiation having a wavelength corresponding to the characteristic absorption line(s) will be partially "absorbed" by the optical radiation. The absorbed portion of the monitored gas is thus prevented from being transmitted therethrough. The amount of the optical radiation that is absorbed is related to the absorption coefficient of the optical radiation at the optical absorption wavelength (s), and the distance travelled by the optical radiation prior to detection of the optical radiation.

Thus, it can be generally stated that the concentration of a gas is related to the optical absorption at the optical absorption wavelength(s). Optical absorption can be quantified by measuring transmission of an optical source at a selected optical absorption wavelength as a function of optical path length. The total transmission of the source light at the selected optical absorption wavelength, for a given optical path length, is given by the following equation (1):

$$T = e^{-ax}, \quad (1)$$

where T is the total transmission of the source light at the selected optical absorption wavelength, a is the absorption coefficient, x is the optical path length, and e is the base for natural logarithms. The value of T will vary in a range of between 0 and 1.

In accordance with the present invention, the value of T over a plurality (n) of different optical path lengths ($x_1-x_n$) is determined by using a plurality (n) of appropriately spaced-apart photodetectors. As will become apparent hereinafter, a novel feature of the present invention resides in the use of multiple detectors and multiple path lengths to simultaneously or sequentially measure optical absorption of the optical radiation over a large dynamic range at reasonably high data collection rates.

Figure 1:
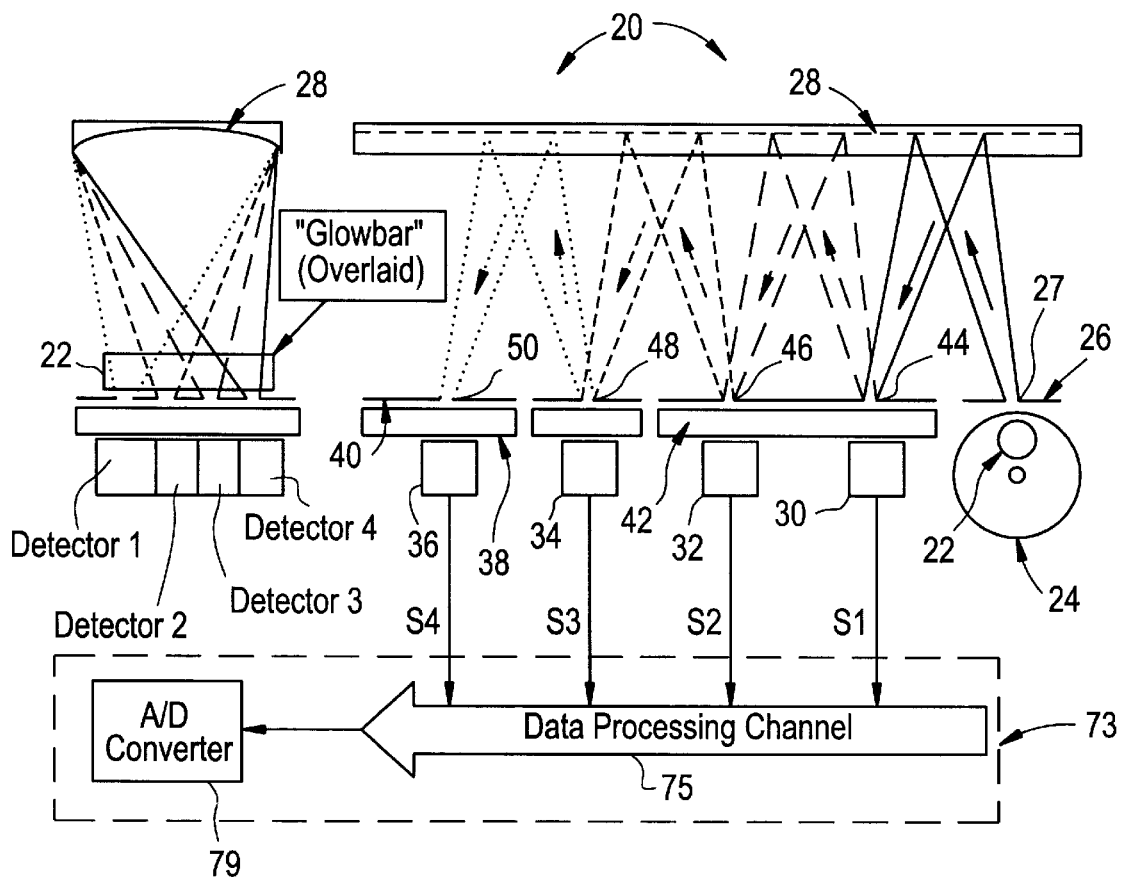
FIG. 1 a diagram that illustrates a gas concentration monitoring system constructed in accordance with a preferred embodiment of the present invention.

With reference now to FIG. 1, there can be seen a diagram of a gas concentration monitoring system 20 constructed in accordance with a preferred embodiment of the present invention. The gas concentration monitoring system 20 includes a cylindrical ("glowbar") optical source 22 mounted within an optical chopper 24, e.g., a multi-windowed rotating drum chopper.

The gas concentration monitoring system 20 further includes a plurality n (e.g., four) photodetectors 30, 32, 34, and 36 that are spaced apart in a linear array opposite a mirror 28 that is preferably provided with a high reflectance coating. A narrow band spectral filter 38 and a detector (or filter) mask 40 having a high reflectance coating are provided on opposite major surfaces of a substrate 42 that is disposed between the mirror 28 and the photodetectors 30, 32, 34, and 36. The substrate 42 is transparent to the selected optical absorption wavelength, and the narrow band spectral filter 38 preferably has a band pass that is matched to the selected optical absorption wavelength. The detector mask 40 is provided with apertures 44, 46, 48, and 50 that are aligned with the photodetectors 30, 32, 34, and 36, respectively.

In operation, the light which exits from the optical chopper 24 passes through a slit (aperture) 27 in a source mask 26 and is reflected one or more times by the mirror 28 and the detector mask 40. In this manner, light that traverses different optical path lengths is provided for detection by the respective photodetectors 30, 32, 34, and 36. More particularly, the optical path length is doubled upon each successive reflection from the mirror 28, so that after the first reflection, the light will have traversed a first optical path length X; after the second reflection, the light will have traversed over a second optical path length 2x; after the fourth reflection, the light will have traversed a third optical path length 4x; and, after the eighth reflection, the light will have traversed a fourth optical path length 8x.

The light that reaches successive ones of the photodetectors 30, 32, 34, and 36 decreases in an exponential manner. For example, in an exemplary implementation of the gas concentration monitoring system 20 to monitor the concentration of CF3I gas in a low concentration (0.3% by volume) in the monitored area, with the first optical path length X=5cm, the measured total transmission T at the first photodetector 30 was 0.993 or 99.3%; the measured total transmission T at the second photodetector 32 was $0.993^2$= 0.987 or 98.7%; the measured total transmission T at the third photodetector 34 was $0.993^4$=0.974 or 97.4%; and, the measured total transmission T at the fourth photodetector 36 was $0.993^8$=0.945 or 94.5%. For a relatively high concentration of CF3I gas of 6.7% by volume, the measured total transmission T at the first photodetector 30 was 85.6%; the measured total transmission T at the second photodetector 32 was 73.2%; the measured total transmission T at the third photodetector 34 was 53.6%; and, the measured total transmission T at the fourth photodetector 36 was 28.7%; From this, it is apparent that the optical path lengths and the band pass of the spectral filters can be selected to optimize the signal-to-noise (S/N) ratio for a particular application.

Figure 2:
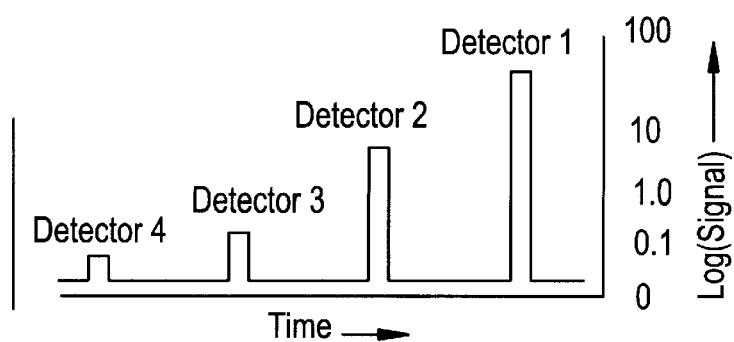
FIG. 2 is a bar graph that depicts the relative signal strength of the outputs of the successive photodetectors of the gas concentration monitoring system depicted in FIG. 1.

From the above, it is apparent that if the total transmission $T_1$ of the optical absorption wavelength over the first (or nominal) optical path is defined as Y, then the total transmission $T_j$ over the successive jth optical path lengths is equal to $Y^{OPj}$, where j=2 through n, and OPj is the nominal optical path length multiple of the jth one of the optical path lengths (e.g., the nominal optical path length multiple of the $3^{rd}$ one of the photodetectors 34 is 4, since the third (jth=$3^{rd}$) optical path length is 4x, where X is the nominal (first)

optical path length). Thus, the relative signal strength of the outputs of the successive photodetectors 30, 32, 34, and 36 can be plotted as an exponential function, as is depicted in FIG. 2.

Figure 3:
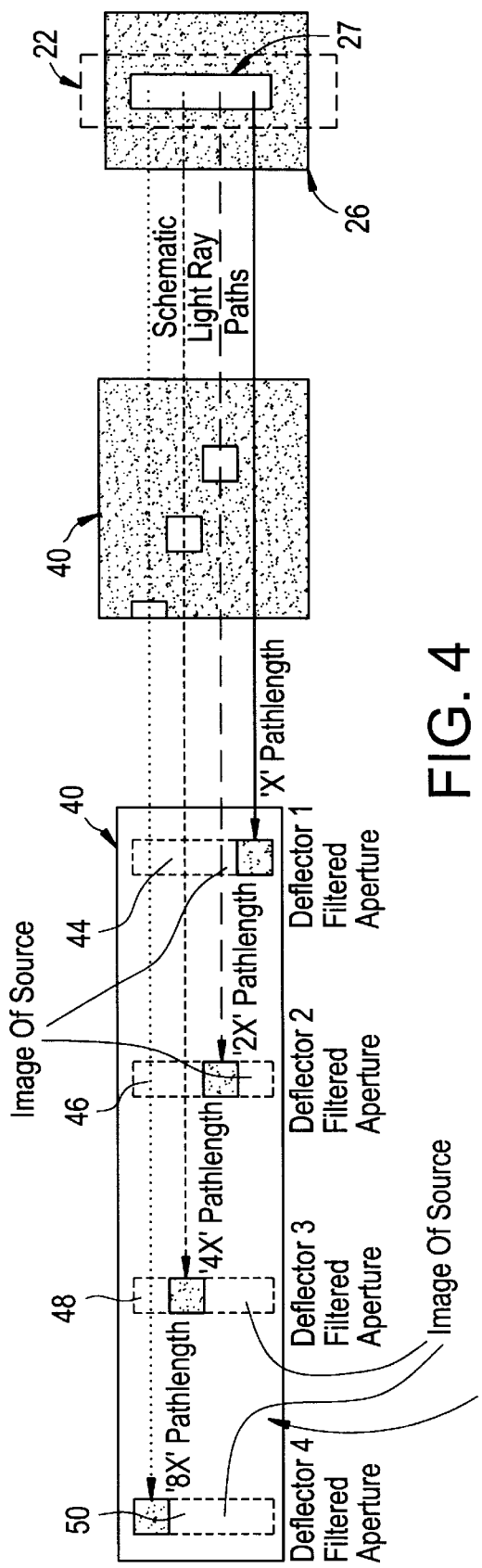
FIG. 3 is a diagram that depicts the layout of the detector (filter) mask and the different optics lengths traversed by the source light that exits from the aperture in the source mask of the gas concentration monitoring system depicted in FIG. 1; and, FIG. 4 is a diagram that depicts the rotating drum chopper that constitutes the optical chopper of an exemplary implementation of the gas concentration monitoring system depicted in FIG. 1.
Figure 4:
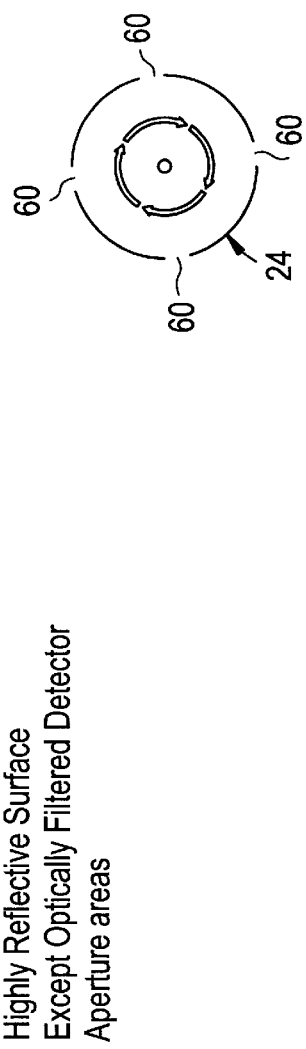

With additional reference to FIG. 3, there can be seen a diagram that depicts the layout of the detector (or filter) mask 40 and the different optical path lengths traversed by the source light that exits from the aperture 27 in the source mask 26. With yet additional reference to FIG. 4, there can be seen a diagram that depicts the rotating drum chopper that constitutes the optical chopper 24 of an exemplary implementation of the gas concentration monitoring system 20 of the present invention. As can be seen, the rotating drum chopper 24 of this exemplary implementation is provided with a plurality n of circumferentially-spaced and laterally displaced apertures or "windows" 60, i.e., the number of windows corresponds to the number of optical path lengths and the number of photodetectors employed, to thereby allow the photodetectors 30, 32, 34, and 36 to receive sequential light pulses and produce sequential output signals in response thereto.

In this exemplary implementation, the mirror 28 is provided with different elliptical or spherical segments that are positioned to receive the light exiting from different respective ones of the windows 60 in the rotating drum chopper 24, so that during each one-quarter revolution of the rotating drum chopper 24, the source light is imaged on a different respective one of the photodetectors 30, 32, 34, and 36. With this scheme, the signal outputs of the photodetectors 30, 32, 34, and 36 are sequential, as is depicted in FIG. 2. As such, the signal processing electronics 73 that processes the signal outputs of the photodetectors (in accordance with well-known algorithms—in order to calculate or "measure" the concentration of the monitored gas) can be simplified.

More particularly, the signal outputs S1, S2, S3, and S4, respectively, of the different photodetectors 30, 32, 34, and 36, can be sequentially switched into a single data processing channel 75 in synchronism with the sequential imaging of the source light on the different photodetectors 30, 32, 34, and 36, thereby enabling the implementation of the signal processing electronics 73 with a single A/D converter 79 and a single data processing channel 75, and without the requirement of an n-to-1 multiplexer or the like. By thus enabling the simplification of the signal processing electronics relative to the presently available technology, the present invention facilitates the manufacture of a simple, compact, and inexpensive, yet fast, accurate, and reliable, gas concentration monitoring device.

However, it should be clearly understood that the present invention also encompasses alternative embodiments in which the source light is essentially simultaneously imaged on each of the photodetectors 30, 32, 34, and 36 (e.g., by using a rotating drum chopper with a single window), with the signal outputs of the photodetectors being processed by signal processing electronics that includes a plurality n of data processing channels (each having a separate A/D converter) and an n-to-1 multiplexer. It will be appreciated that with the latter scheme, the power of the light source must be sufficiently high to ensure that the amount of light that reaches each of the photodetectors is sufficiently above the noise floor of the photodetectors to ensure an adequate S/N ratio for the signal processing electronics.

In the above-described exemplary implementation, the rate of rotation of the rotating drum chopper 24 is ten (10) revolutions per second (rps), although this is, of course, not limiting to the present invention. With this exemplary implementation, a total of forty (40) different signal outputs will be produced by the photodetectors 30, 32, 34, and 36 per second, which outputs can be used by the signal processing electronics to produce 40 independent measurements of the concentration of the optical radiation in the monitored sample per second and/or a lesser number of correlated (e.g., statistically averaged) measurements of the concentration of the monitored gas in the monitored sample per second.

Thus, the gas concentration monitoring system 20 of the present invention enables the monitoring of a single sample position in a rapid and highly accurate manner. Also, the gas concentration monitoring system 20 of the present invention features high data collection rates and a large dynamic range. Further, since the gas concentration monitoring system 20 of the present invention utilizes a single optical source and multiple detectors arranged in a short linear array along multiple optical path lengths, as well as greatly simplified signal processing electronics, it can be easily implemented in a single, compact device that is capable of being flown on an aircraft. Many such systems can be installed within a test area to monitor concentration and distribution of the optical radiation. In a presently contemplated application, the gas concentration monitoring system of the present invention will be used to measure the concentration levels over time of a fire suppression agent (e.g., CF3I or HF-25) in the engine bays and/or cargo holds of military and civilian aircraft for certification (qualification) and/or dynamic monitoring of the fire suppression systems of such aircraft.

Although the present invention has been described in detail hereinabove, it should be clearly understood that many variations and/or modifications of the basic inventive concepts taught herein that may become apparent to those skilled in the pertinent art will still fall within the spirit and scope of the present invention as defined in the appended claims.

For example, although the gas concentration monitoring system 20 of the preferred embodiment employs a broadband light source and an optical chopper to provide the source light that is utilized in the system for measuring the concentration of the monitored gas, it will be readily apparent to those skilled in the pertinent art that a narrow band or coherent, monochromatic light source that is designed to produce light at the optical absorption wavelength can be utilized instead. Alternatively, the narrow band spectral filter 38 can be placed adjacent the aperture 27 in the source mask 26 rather than adjacent the detector (filter) mask 40, to thereby filter the light prior to its being reflected from the mirror 28. Also, rather than an optical chopper, any other suitable light modulation mechanism can be utilized. Of course, many other variations and/or modifications are possible without departing from the spirit and scope of the present invention as defined in the appended claims.

What is claimed is:

1. A system for monitoring the concentration level of a gas in a monitored environment, comprising:

means for producing light;

means for directing the light along a plurality of different optical paths having different respective optical path lengths;

means for filtering the light to pass only a prescribed spectral band which includes an optical absorption wavelength of the gas;

means for detecting the filtered light that traverses each different optical path length, and for producing a plurality of output signals indicative of the concentration level of the gas in the monitored environment;

wherein the means for producing light includes a cylindrical optical source;

wherein the means for directing includes a plurality of photodetectors that are positioned to receive the filtered light that traverses different respective ones of the plurality of different optical path lengths; and, wherein the means for directing the light includes:
   a multi-windowed rotating optical chopper that contains the optical source and produces a repeating sequence of light pulses that traverse successive ones of the plurality of different optical path lengths;
   a mirror;
   a detector mask that is positioned between the mirror and the plurality of photodetectors; and,
   wherein the detector mask includes a substrate that is transparent to the optical absorption wavelength of the gas, the substrate having a first major surface coated with a reflective material and having a plurality of apertures aligned with respective ones of the plurality of photodetectors, wherein the mirror and the reflective material of the first major surface of the substrate, in combination, reflect the sequential light pulses to traverse the plurality of different optical path lengths.

2. The system as set forth in claim 1, wherein the means for directing the light includes:
   optical modulator means for modulating the light produced by the means for producing light in such a manner as to produce a repeating sequence of light pulses that traverse successive ones of the plurality of different optical path lengths; and,
   mirror means for reflecting the sequential light pulses to traverse the plurality of different optical path lengths.

3. The system as set forth in claim 1, wherein the means for detecting includes a plurality of photodectors that are positioned to receive the filtered light that traverses different respective ones of the plurality of different optical path lengths.

4. The system as set forth in claim 3, wherein the means for directing light further includes a source mask having an aperture that is positioned to allow the sequential light pulses to pass therethrough.

5. The system as set forth in claim 1, wherein the means for filtering the light includes a narrow band spectral filter provided on a second major surface of the substrate opposite the first major surface.

6. The system as set forth in claim 1, wherein the monitored environment includes the engine bay or cargo compartment of an aircraft and the gas is a fire suppression agent.

7. The system as set forth in claim 1, wherein each successive optical path length is double the previous optical path length.

8. A system for monitoring the concentration level of a gas in a monitored environment, comprising:
   means for producing monochromatic light having a wavelength that is the same as a selected optical absorption wavelength of the gas;
   means for directing the light along a plurality of different optical paths having different respective optical path lengths;
   photodetecting means for detecting the light that traverses each different optical path length, and for producing a plurality of respective output signals indicative of the concentration level of the gas in the monitored environment; and
   a single channel data processing means for processing the plurality of output signals produced by the photodetecting means.

9. A system for monitoring the concentration level of a gas in a monitored environment, comprising:
   a light source for producing source light;
   an optical system that directs the source light along a plurality of different optical paths having different respective optical path lengths;
   a plurality of photodetectors that are positioned to receive the source light that traverses different respective ones of the plurality of different optical path lengths, and which produce a plurality of output signals indicative of the concentration level of the gas in the monitored environment;
   a narrow band spectral filter means positioned between the light source and each photodetector, wherein the narrow band spectral filter means has a narrow band pass that is the same for each photodetector, and that is matched to a selected optical absorption wavelength of the gas; and,
   a single-channel data processing means for processing the plurality of output signals.

10. A method for monitoring the concentration level of a gas in a monitored environment, comprising:
   providing a plurality of photodetectors;
   directing light along a plurality of different optical paths having different respective optical path lengths;
   filtering the light to pass only a prescribed spectral band which includes an optical absorption wavelength of the gas, which is the same spectral band for the light that traverses each different optical path length;
   detecting the filtered light that traverses each different optical path length with a respective photodetector, and said plurality of photodetectors producing a plurality of output signals indicative of the concentration level of the gas in the monitored environment; and
   processing the plurality of output signals produced by the photodetectors using a single channel data processing means.

11. The method as set forth in claim 10, the step of directing the light is carried out by modulating the source light in such a manner as to produce a repeating sequence of light pulses that traverse successive ones of the plurality of different optical path lengths.

12. The method as set forth in claim 10, wherein the monitored environment includes the engine bay or cargo compartment of an aircraft and the gas is a fire suppression agent.

13. A method for monitoring the concentration level of a gas in a monitored environment, comprising the steps:
   providing a plurality of photodetectors;
   producing monochromatic light having a wavelength that is the same as a selected optical absorption wavelength of the gas;
   directing the light along a plurality of different optical paths having different respective optical path lengths; and
   detecting the light that traverses each different optical path length with a respective photodetector, and said plurality of photodetectors producing a plurality of output signals indicative of the concentration level of the gas in the monitored environment; and
   processing the plurality of output signals produced by the photodetectors using a single channel data processing means.

14. The method as set forth in claim 13, wherein the monitored environment includes the engine bay or cargo compartment of an aircraft and the gas is a fire suppression agent.

15. A system for monitoring the concentration level of a gas in a monitored environment, comprising:

means for producing light;

means for directing the light along a plurality of different optical paths having different respective optical path lengths;

means for filtering the light to pass only a prescribed spectral band which includes an optical absorption wavelength of the gas;

means for detecting the filtered light that traverses each different optical path length, and for producing a plurality of output signals indicative of the concentration level of the gas in the monitored environment;

wherein the means for producing light includes a cylindrical optical source;

wherein the means for directing includes a plurality of photodetectors that are positioned to receive the filtered light that traverses different respective ones of the plurality of different optical path lengths; and, wherein the means for directing the light includes:

a rotating drum chopper that contains the cylindrical optical source and that is provided with a plurality n of circumferentially-spaced and laterally displaced windows, where n is equal to the number of different optical path lengths and the number of photodetectors, whereby the rotating drum chopper produces a repeating sequence of light pulses;

a mirror that is provided with n different segments that are positioned to reflect different respective ones of the sequential light pulses to traverse different respective ones of the optical path lengths; and, wherein during each 1/n revolution of the rotating drum chopper, the light from the optical source is imaged on a different respective one of the photodetectors.

16. The system as set forth in claim 15, wherein the monitored environment includes the engine bay or cargo compartment of an aircraft and the gas is a fire suppressant agent.

\* \* \* \* \*